US011227384B2

(12) United States Patent
Kashyap et al.

(10) Patent No.: US 11,227,384 B2
(45) Date of Patent: Jan. 18, 2022

(54) METHODS AND SYSTEMS FOR DETERMINING A DIAGNOSTICALLY UNACCEPTABLE MEDICAL IMAGE

(71) Applicant: INTERNATIONAL BUSINESS MACHINES CORPORATION, Armonk, NY (US)

(72) Inventors: Satyananda Kashyap, San Jose, CA (US); Alexandros Karargyris, San Jose, CA (US); Joy Wu, Mountain View, CA (US); Mehdi Moradi, San Jose, CA (US); Tanveer Fathima Syeda-Mahmood, Cupertino, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 352 days.

(21) Appl. No.: 16/272,652

(22) Filed: Feb. 11, 2019

(65) Prior Publication Data
US 2020/0258215 A1    Aug. 13, 2020

(51) Int. Cl.
*G06T 7/00* (2017.01)
*G06K 9/62* (2006.01)
(Continued)

(52) U.S. Cl.
CPC ............ *G06T 7/0012* (2013.01); *G06K 9/627* (2013.01); *G06N 3/08* (2013.01); *G06N 20/00* (2019.01);
(Continued)

(58) Field of Classification Search
CPC ....... G06T 7/0002; G06T 7/0012; G06T 7/11; G06T 2207/30061; G06T 2207/10116;
(Continued)

(56) References Cited

U.S. PATENT DOCUMENTS 5,987,094 A    11/1999  Clarke et al.
10,098,215 B2  10/2018  Nakahara et al.
(Continued)

FOREIGN PATENT DOCUMENTS

CN    106909778 A    6/2017
DE    10332834 A1    2/2005

OTHER PUBLICATIONS

Little, K. J. et al., "Unified Database for Rejected Image Analysis Across Multiple Vendors in Radiography", Journal of the American College of Radiology, (2017).
(Continued)

*Primary Examiner* — Nay A Maung
*Assistant Examiner* — Jose M Torres
(74) *Attorney, Agent, or Firm* — Michael Best & Friedrich LLP

(57) ABSTRACT

Methods and systems for determining a diagnostically unacceptable medical image. One system includes at least one electronic processor configured to receive a new medical image captured via a medical imaging device. The at least one electronic processor is also configured to determine a classification of the new medical image using a model developed with machine learning using training information that includes a plurality of medical images and an associated classification for each medical image, each associated classification identifying whether the associated medical image is diagnostically unacceptable, wherein the classification of the new medical image indicates whether the new medical image is diagnostically unacceptable. The at least one electronic processor is also configured to, when the classification indicates that the new medical image is diagnostically unacceptable, prompt a user of the medical imaging device to adjust a parameter associated with the new medical image and recapture the new medical image.

17 Claims, 14 Drawing Sheets
(10 of 14 Drawing Sheet(s) Filed in Color)

(51) Int. Cl.
  *G06N 20/00* (2019.01)
  *G16H 30/00* (2018.01)
  *G06N 3/08* (2006.01)
(52) U.S. Cl.
  CPC ... G16H 30/00 (2018.01); *G06T 2207/30061* (2013.01)
(58) Field of Classification Search
  CPC ........... G06T 2207/20081; G06T 2207/20084; G06K 9/627; G06K 9/6273; G06K 2209/05; G06N 3/006; G06N 3/0454; G06N 3/08; G06N 3/126; G06N 5/003; G06N 20/00; G06N 20/10; G16H 30/00; G16H 30/20; G16H 30/40; G16H 50/20
  See application file for complete search history.

(56) References Cited

U.S. PATENT DOCUMENTS

| | | | | |
|---|---|---|---|---|
| 2006/0239522 | A1* | 10/2006 | Ferrant | G06T 7/12 382/128 |
| 2006/0274145 | A1* | 12/2006 | Reiner | G16H 30/20 348/62 |
| 2019/0156484 | A1* | 5/2019 | Nye | G16H 50/20 |
| 2019/0228547 | A1* | 7/2019 | Chandarana | G06N 3/0481 |
| 2020/0043616 | A1* | 2/2020 | Saalbach | G16H 30/40 |
| 2020/0089983 | A1* | 3/2020 | Manickam | G06T 7/0012 |
| 2020/0160511 | A1* | 5/2020 | Lyman | G06F 21/6254 |

OTHER PUBLICATIONS

Fintelmann, F. et al., "Repeat rates in digital chest radiography and strategies for improvement", Journal of Thoracic Imaging, (2012).
Hofmann, B. et al., "Image rejects in general direct digital radiography", Acta Radiologica Short Reports, (2015).
Jones, A. K. et al., "One year's results from a server-based system for performing reject analysis ahd exposure analysis in computed radiography", Journal of Digital Imaging. (2011).
Taylor, N., "The art of rejection: Comparative analysis between Computed Radiography (CR) and Digital Radiography (DR) workstations in the Accident & Emergency and General radiology departments at a district general hospital using customized and standardized reject cr", Radiography, (2015).
Rajpurkar, P. et al., "CheXNet: Radiologist-Level Pneumonia Detection on Chest X-Rays with Deep Learning", arXiv preprint arXiv:1711.05225, (2017).
Islam, M. T. et al., "Abnormality Detection and Localization in Chest X-Rays using Deep Convolutional Neural Networks", CoRR abs/1705.0, (2017).
Shin, H. C. et al., "Learning to Read Chest X-Rays: Recurrent Neural Cascade Model for Automated Image Annotation", In: 2016 IEEE Conference on Computer Vision and Pattern Recognition (CVPR), (2016).
Wang, X. et al., "ChestX-ray8: Hospital-scale chest X-ray database and benchmarks on weakly-supervised classification and localization of common thorax diseases", In: Proceedings—30th IEEE Conference on Computer Vision and Pattern Recognition, CVPR 2017, (2017).
Wang, X. et al., "TieNet: Text-Image Embedding Network for Common Thorax Disease Classification and Reporting in Chest X-rays", Corr abs/1801.0, (2018).
Huang, G. et al., Densely connected convolutional networks, In: Proceedings—30th IEEE Conference on Computer Vision and Pattern Recognition, CVPR 2017, (2017).
Ronneberger, O. et al., "U-net: Convolutional networks for biomedical image segmentation", Lecture Notes in Computer Science (including subseries Lecture Notes in Artificial Intelligence and Lecture Notes in Bioinformatics), 9351 (2015), pp. 234-241.
Chollet, F., "Keras Documentation", Keras.Io, (2015).
Abadi, M. et al., "TensorFlow: Large-Scale Machine Learning on Heterogeneous Distributed Systems", (2015).
Pedregosa, F., "Scikit-learn: Machine Learning in Python", Journal of MAchine Learning Research, (2011).
Mettler, F. A. et al., "Radiologic and Nuclear Medicine Studies in the United States and Worldwide: Frequency, Radiation Dose, and Comparison with Other Radiation Sources 19502007", Radiology 253, pp. 520-531, (Nov. 2009).
Owusu-Banahene, J. et al., "Film reject analysis and image quality in diagnostic Radiology Department of a Teaching hospital in Ghana", Journal of Radiation Research and Applied Sciences, (2014).
Abubakar Audu, S. et al., "X-ray Film Reject Analysis as a Quality Indicator in a Tertiary Health Center in Northwestern Nigeria", (2017).
Jabbari, N., "Patient dose from radiographic rejects/repeats in radiology centers of Urmia University of Medical Sciences, Iran", Health 04, pp. 94-100, (Feb. 2012).
Bassey, C. E. et al., "Repeat profile analysis in an x-ray department", Journal of Radiological Protection, (1991).
Watkinson, S. et al., "Reject analysis: its role in quality assurance", Radiography 50(593), pp. 189-194, Year: 1984.
Dunn, M. A. et al., "X-ray film reject analysis as a quality indicator", Radiography 4, pp. 29-31, (Feb. 1998).
Zewdu, M. et al., "Analysis and Economic Implication of X-Ray Film Reject in Diagnostic Radiology Department of Jimma University Specialized Hospital, Southwest Ethiopia", Ethiopian Journal of Health Sciences 27, pp. 421-426, (Jul. 2017).
Teferi, S. et al., The Ethiopian journal of health development, vol. 26, National Health Development Network—Ethiopia, Year: 2010.
Ofori, E. et al., "Analysis and Economic Implications of X-ray Film Repeat/Reject in Selected Hospitals in Ghana", West African Journal of Radiology 20(1), 14, (2013).
Usha, M. et al., "Reject Analysis in Conventional Radiography", Nepalese Journal of Radiology 3, pp. 65-67, (Jan. 2014).
"Radiology Protection in Radiology", Year: 2019.
Santosh, K. C., et al., "Rotation detection in chest radiographs based on generalized line histogram of rib-orientations", Proceedings—IEEE Symposium on Computer-Based Medical Systems, pp. 138-142, IEEE, (May 2014).
Rubin, J. et al., "Large Scale Automated Reading of Frontal and Lateral Chest X-Rays Using Dual Convolutional Neural Networks", arXiv preprint arXiv: 1804.07839, (2018).
Laserson, J. et al., "TextRay: Mining clinical reports to gain a broad understanding of chest X-rays", Lecture Notes in Computer Science ) including subseries Lecture Notes in Artificial Intelligence and Lecture Notes in Bioinformatics, (2018).
Deng, J. et al., "ImageNet: A large-scale hierarchical image database", 2009 IEEE Conference on COmputer Vision and Pattern Recognition, (2009).

* cited by examiner

METHODS AND SYSTEMS FOR DETERMINING A DIAGNOSTICALLY UNACCEPTABLE MEDICAL IMAGE

FIELD

Embodiments described herein relate to methods and systems for determining a diagnostically unacceptable medical image, and more particularly, to automatically determining a diagnostically unacceptable medical image, such as a diagnostically unacceptable chest radiograph, at the point of image acquisition using machine learning.

SUMMARY

X-ray radiograph is the most common imaging modality in the United States. In fact, chest X-rays are among the most common modalities in medical imaging. X-ray radiograph makes up 74% of all imaging modalities ordered by physicians. In 2006, over 100 million chest X-rays were taken in the United States, which accounted for 46% of all the X-ray exams.

The quality of an X-ray imaged is important to help the radiologist diagnose a patient's condition accurately. Technical flaws of these images, such as over- or under-exposure or wrong positioning of the patients, may result in a decision to reject and repeat the scan, which wastes resources and patient time as well as delays diagnoses. A reject rate of a scan is defined as the number of scans of the anatomy seen by a technologist but not shown to the radiologist. In the United States, the overall reject rate for standard radiographs in a hospital ranges from 8-27%. Amongst rejected X-ray exams, chest X-rays account for the largest proportion of the rejections (up to 38%). In some institutions, the X-ray reject rate is above the 5% recommended by the World Health Organization (WHO).

Reducing the rejection rate due to technical quality issues can result in cost savings for hospitals and increased operational efficiencies. It can also reduce delays in patient workup and improved quality of care. In particular, repeating a rejected exam out of the normal imaging workflow involves calling the patients back or asking the technician to return to the bedside to rescan the patients, both of which cause time consuming disruptions to the work-flow.

Although digital radiography has reduced the reject rate from the earlier X-ray film technology, there are still common positioning errors, which cannot simply be resolved with image contrast or brightness adjustments. These errors include rotation or tilting of the patient's body relative to the X-ray beam. Severe rotation results in abnormal projection of the anatomies in the chest, distorting the diagnostic qualities of the film. The tilting of the body can result in parts of the lungs to be cut off from the field of view, leading to an incomplete exam, which carries medical legal risks for a radiologist to accept and report on.

Besides positioning errors, a variety of X-ray technical quality issues also result in distinct imaging features (e.g., limited field of view, etc.). This variety makes the task of recognizing technically non-diagnostic images at the initial point of acquisition difficult as this recognition must be performed quickly and accurately while the X-ray machine is operational and calibrated to avoid the problems with rejections and rescans.

Accordingly, to solve these and other problems, embodiments described herein provide methods and systems to detect medical images (for example, chest radiographs) that are not suitable for diagnostic study. In particular, to alleviate the burden on technicians and to assist in the decision making of rejected scans, embodiments described herein aid radiographers and technicians in the technical assessment of radiographs in an earlier part of the radiology work-flow (at point of image acquisition) to improve subsequent operational efficiencies and quality of care. When deployed at the point of image acquisition, such methods and systems can warn the technician acquiring the medical images, so a repeat image may be acquired without the need to bring the patient back to the scanner. In other words, embodiments described herein provide methods and systems for identifying technical human errors (as compared to machine or equipment errors) that result in poor diagnostic quality images, such as a limited field of view, patient rotation and the like, while the X-ray machine is operational and calibrated.

For example, one embodiment provides a system for determining a diagnostically unacceptable medical image. The system includes at least one electronic processor configured to receive a new medical image captured via a medical imaging device, the new medical image associated with a patient. The at least one electronic processor is also configured to determine a classification of the new medical image using a model developed with machine learning using training information, the training information including a plurality of medical images and an associated classification for each of the plurality of medical images, each associated classification identifying whether the associated medical image is diagnostically unacceptable, wherein the classification of the new medical image indicates whether the new medical image is diagnostically unacceptable. The at least one electronic processor is also configured to, when the classification of the new medical image indicates that the new medical image is diagnostically unacceptable, prompt a user of the medical imaging device to adjust a parameter associated with the new medical image and recapture the new medical image using the adjusted parameter.

Another embodiment provides a method for determining a diagnostically unacceptable medical image. The method includes receiving, with at least one electronic processor, a first medical image captured via a medical imaging device, the first medical image associated with a patient. The method also includes determining, with the at least one electronic processor, a classification of the first medical image using a model developed with machine learning using training information, the training information including a plurality of medical images and an associated classification for each of the plurality of medical images, each associated classification identifying whether the associated medial image is diagnostically unacceptable, wherein the classification of the first medical image indicates that the first medical image is diagnostically unacceptable. The method also includes outputting, via a display device of the medical imaging device, a first message to a user of the medical imaging device, the first message prompting the user to adjust at least one parameter associated with the first medical image and to capture a second medical image using the at least one adjusted parameter. The method also includes receiving the second medical image captured via the medical imaging device using the at least one adjusted parameter. The method also includes determining, with the at least one electronic processor, a classification of the second medical image using the model, the classification of the second medical image indicating that the second medical image is diagnostically acceptable. The method also includes outputting, via the display device, a second message to the user of the medical imaging device, the second message prompting the user to store the second medical image.

Another embodiment provides a non-transitory, computer-readable medium storing instructions that, when executed by an electronic processor, perform a set of functions. The set of functions includes receiving a first medical image captured via a medical imaging device, the first medical image associated with a patient. The set of functions also includes determining a classification of the first medical image using a model, the classification indicating whether the first medical image is diagnostically unacceptable, the model developed based on training information, the training information including a plurality of medical images and an associated classification for each of the plurality of medical images, each associated classification identifying whether the associated medical image is diagnostically unacceptable. The set of functions also includes outputting a message, the message prompting a user, based on the classification of the first medical image, to either (a) store the first medical image or (b) adjust a parameter associated with the first medical image and capture a second medical image based on the adjusted parameter.

Other aspects of the embodiments described herein will become apparent by consideration of the detailed description and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
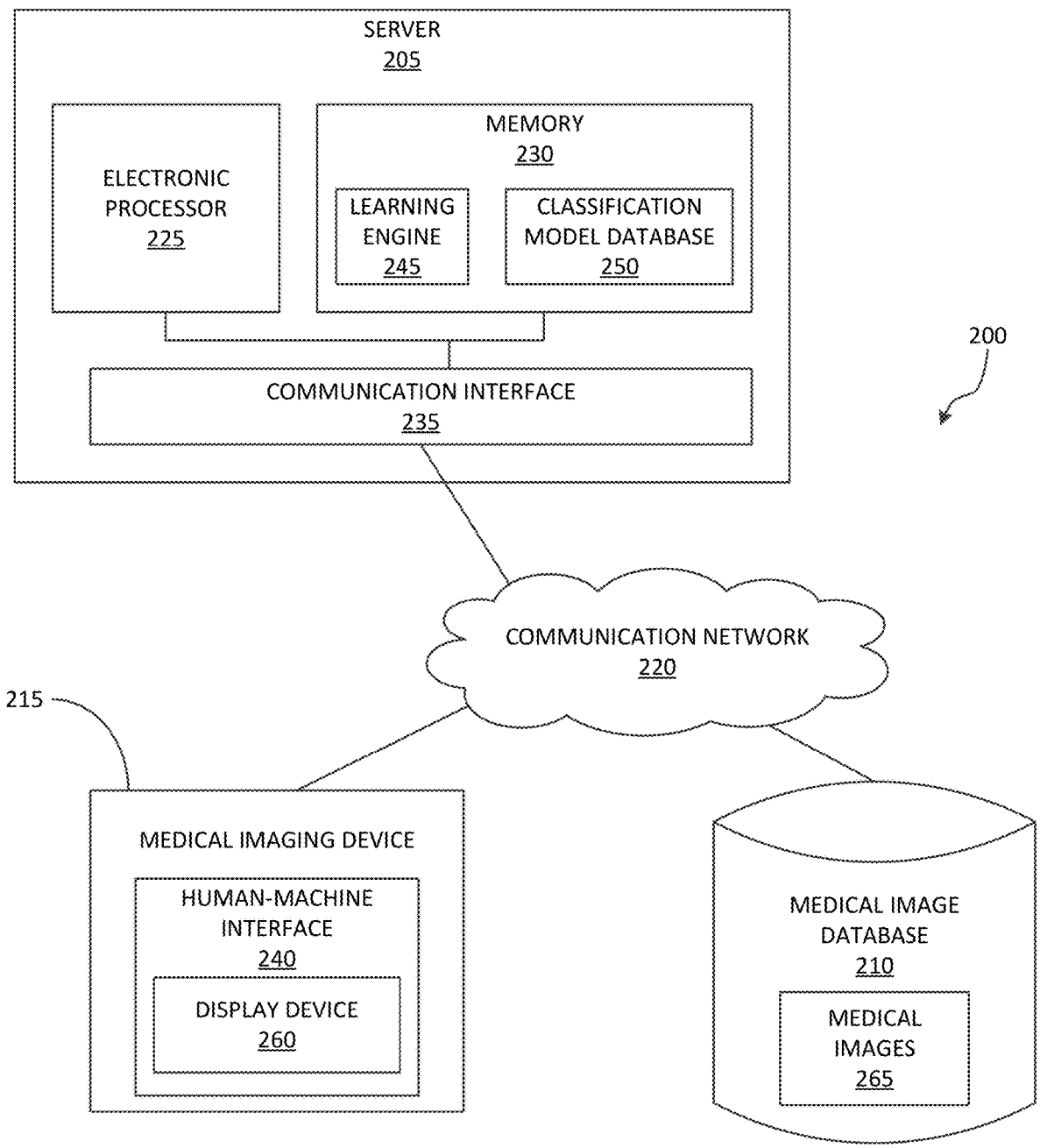
FIG. 1 illustrates a system of determining a diagnostically unacceptable image according to some embodiments.

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used herein, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

As described above, the quality of a medical image, such as an X-ray image, is important to help a radiologist diagnose a patient's condition accurately. Technical flaws ("technical defects") of these images caused by technical human errors, such as over- or under-exposure or wrong positioning of a patient, may result in a decision to reject and repeat the scan, which wastes resources.

Accordingly, embodiments described herein present a new use of artificial intelligence ("AI") algorithms to aid radiographers and technicians in the technical assessment of radiographs in an earlier part of the radiology workflow to improve the subsequent operational efficiencies and quality of care. Embodiments described herein address the problem as a multi-class classification problem, which simultaneously detects several types of technical defects in an X-ray. Embodiments described herein are described with respect to chest radiographs as they are common in X-ray imaging. In addition, chest X-rays are often fraught with visually recognizable positional errors. For example, given the various set of complicated organs that exist in the chest, a mispositioned patient may lead to the projected X-ray shadows being distorted and wrongly interpreted as an enlarged organ. Additionally, an incomplete field of view may lead to missing some life-threatening diseases in corners of the lungs or the chest region, such as a cancerous mass or nodule.

FIG. 1 illustrates a system 200 for determining a diagnostically unacceptable medical image at point of image acquisition according to some embodiments. The system 200 includes a server 205, a medical image database 210, and a medical imaging device or modality 215. In some embodiments, the system 200 includes fewer, additional, or different components than illustrated in FIG. 1. For example, the system 200 may include multiple servers 205, medical image databases 210, medical imaging devices 215, or a combination thereof.

The server 205, the medical image database 210, and the medical imaging device 215 communicate over one or more wired or wireless communication networks 220. Portions of the communication network 220 may be implemented using a wide area network, such as the Internet, a local area network, such as a Bluetooth™ network or Wi-Fi, and combinations or derivatives thereof. Alternatively or in addition, in some embodiments, components of the system 200 communicate directly as compared to through the communication network 220. Also, in some embodiments, the components of the system 200 communicate through one or more intermediary devices not illustrated in FIG. 1.

The server 205 is a computing device, which may serve as a gateway for the medical image database 210. For example, in some embodiments, the server 205 may be a commercial picture archive and communication system (PACS) server. Alternatively, in some embodiments, the server 205 may be a server that communicates with a PACS server to access the medical image database 210. As illustrated in FIG. 1, the server 205 includes an electronic processor 225, a memory 230, and a communication interface 235. The electronic processor 225, the memory 230, and the communication interface 235 communicate wirelessly, over one or more communication lines or buses, or a combination thereof. The server 205 may include additional components than those illustrated in FIG. 1 in various configurations. The server 205 may also perform additional functionality other than the functionality described herein. Also, the functionality described herein as being performed by the server 205 may be distributed among multiple devices, such as multiple servers included in a cloud service environment. In addition, in some embodiments, the medical imaging device 215 may be configured to perform all or a portion of the functionality described herein as being performed by the server 205.

The electronic processor 225 includes a microprocessor, an application-specific integrated circuit ("ASIC"), or another suitable electronic device for processing data. The memory 230 includes a non-transitory computer-readable medium, such as read-only memory ("ROM"), random access memory ("RAM") (for example, dynamic RAM ("DRAM"), synchronous DRAM ("SDRAM"), and the like), electrically erasable programmable read-only memory ("EEPROM"), flash memory, a hard disk, a secure digital ("SD") card, another suitable memory device, or a combination thereof. The electronic processor 225 is configured to access and execute computer-readable instructions ("software") stored in the memory 230. The software may include firmware, one or more applications, program data, filters, rules, one or more program modules, and other executable instructions. For example, the software may include instructions and associated data for performing a set of functions, including the methods described herein.

For example, as illustrated in FIG. 1, the memory 230 may store a learning engine 245 and a classification model database 250. It should be understood that in some embodiments, the classification model database 250 may be located external to the server 205. In this embodiment, the server 205 may communicate with and access data from the classification model database 250 directly or through one or more of the communication network(s) 220. Also, in some embodiments, the classification model database 250 may be included in or part of the medical image database 210, the medical imaging device 215, or a combination thereof, which the server 205 may similarly access.

The communication interface 235 allows the server 205 to communicate with devices external to the server 205. For example, as illustrated in FIG. 1, the server 205 may communicate with the medical image database 210 through the communication interface 235. In particular, the communication interface 235 may include a port for receiving a wired connection to an external device (for example, a universal serial bus ("USB") cable and the like), a transceiver for establishing a wireless connection to an external device (for example, over one or more communication networks 220, such as the Internet, local area network ("LAN"), a wide area network ("WAN"), and the like), or a combination thereof.

The medical imaging device 215 is a user device configured to capture medical images, such as an X-ray machine. Although not illustrated, the medical imaging device 215 may include similar components as the server 205 (an electronic processor, a memory, and a communication interface) in addition to medical imaging components for capturing medical images. As noted above, in some embodiments, a memory of the medical imaging device 215 may store the classification model database 250. Alternatively or in addition to, the medical imaging device 215 may access the classification model database 250 stored in the memory 230 of the server 205 (or another device external to the medical image device 215) via the communication network 220.

The medical imaging device 215 may also include a human-machine interface 240. The human-machine interface 240 may include one or more input devices, one or more output devices, or a combination thereof. Accordingly, in some embodiments, the human-machine interface 240 allows a user to interact with (for example, provide input to and receive output from) the medical imaging device 215. For example, the human-machine interface 240 may include a keyboard, a cursor-control device (for example, a mouse), a touch screen, a scroll ball, a mechanical button, a display device (for example, a liquid crystal display ("LCD")), a printer, a speaker, a microphone, or a combination thereof. As illustrated in FIG. 1, in some embodiments, the human-machine interface 240 includes a display device 260. The display device 260 may be included in the same housing as the medical imaging device 215 or may communicate with the medical imaging device 215 over one or more wired or wireless connections. For example, in some embodiments, the display device 260 is a touchscreen included in a laptop computer or a tablet computer. In other embodiments, the display device 260 is a monitor, a television, or a projector coupled to a terminal, desktop computer, or the like via one or more cables.

The medical image database 210 stores a plurality of medical images 265. In some embodiments, the medical image database 210 is combined with the server 205. Alternatively or in addition, the medical images 265 may be stored within a plurality of databases, such as within a cloud service. Although not illustrated in FIG. 1, the medical image database 210 may include components similar to the server 205, such as an electronic processor, a memory, a communication interface, and the like. For example, the medical image database 210 may include a communication interface configured to communicate (for example, receive data and transmit data) over the communication network 220.

In some embodiments, the medical image database 210 stores additional data associated with the medical images 265, such as a classification associated with each of the medical images 265 and one or more technical defects associated with one or more of the medical images 265 as described below in more detail. Accordingly, in some embodiments, the medical image database 210 stores the training information used to train the classification models stored in the classification model database 250. In other embodiments, this information (along with the associated image data) may be stored separate from the medical image database 210. However, the medical image database 210 may store acquired or captured medical images ("new medical images" distinguished from the images included in the training information) captured via the medical imaging device 215.

A user (i.e., a technician) may use the medical imaging device 215 to capture one or more medical images associated with a patient. For example, the technician may capture a new medical image using the medical imaging device 215 and view the new medical image (as a preview) on the display device 260 of the medical imaging device 215. As noted above, the new medical image may be diagnostically unacceptable due to one or more technical defects. However, if the technician does not identify the defects, a reading radiologist may later detect the defects, which one or more technical defects may not be identifiable until a later point in time, such as when the reading radiologist analyzes the new medical image. Thus, in this situation, the technician may be instructed to recapture the new medical image. To solve this and other problems, the system 200, as described in more detail below, is configured to automatically determine a diagnostically unacceptable medical image at the point of image acquisition (e.g., when the medical image is first captured using the medical imaging device 215). Based on whether the medical image is classified as diagnostically unacceptable or diagnostically acceptable, the technician may be prompted to save the medical image, such as to the medical image database 210, or recapture the medical image with adjusted parameters using the medical imaging device 215.

For example, in some embodiments, the learning engine 245 (when executed by the electronic processor 225) develops a classification model using one or more machine learning functions, and classification models generated by the learning engine 245 may be stored in the classification model database 250. A developed classification model can then be used to determine diagnostically unacceptable images at the point of imaging (the medical imaging device 215).

Machine learning functions are generally functions that allow a computer application to learn without being explicitly programmed. In particular, a computer application performing machine learning functions (sometimes referred to as a learning engine) is configured to develop an algorithm based on training data (or training information). For example, to perform supervised learning, the training data includes example inputs and corresponding desired (for example, actual) outputs, and the learning engine progressively develops a model (for example, a classification model) that maps inputs to the outputs included in the training data. Machine learning may be performed using various types of methods and mechanisms including but not limited to decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using all of these approaches, a computer program may ingest, parse, and understand data and progressively refine models for data analytics, including image analytics.

Accordingly, the learning engine 245 (as executed by the electronic processor 225) performs machine learning using training data (images accessed from the medical image database 210) to develop a classification model that maps medical images 265 to one or more classifications. The training data may include, for example, medical images and their associated classifications. For example, the learning engine 245 may identify one or more unique characteristics of a medical image (for example, one or more technical defects associated in the medical image) and develop a classification model that maps the one or more unique characteristics to a particular classification, such as either diagnostically unacceptable or diagnostically acceptable. Accordingly, when a subsequent medical image is received, the developed classification model may be used to determine a classification for that subsequent medical image. In other words, the classification model, once trained, analyzes content of a medical image to identify one or more technical defects in the medical image and assign the medical image a classification based on any detected technical defects. As described in more detail below, in some embodiments, the classification model is applied to images at the point of image acquisition with the medical imaging device 215.

In some embodiments, the training information includes a set of medical images, wherein at least a subset of the set of medical images includes at least one technical defect and each medical image in the set includes a classification. Table 1, provided below, includes a list of different technical defects. These technical defects occur due to human operator-based error on calibrated and functioning X-ray systems. Note that the "Clear Label" indicates an error free X-ray that has no technical defects caused by human error. The "Clear Label" does not indicate an absence of the disease.

TABLE 1

| Listing of Technical Defects |
| --- |
| Clear Label |
| Apical Kyphotic |
| Apical Lordotic |
| Apices Not Included |
| Body Rotated to the Left |
| Body Rotated to the Right |
| Body Slanted to the Left |
| Body Slanted to the Right |
| Costophrenic Angles Not Included |
| Diagnostic |
| Diaphragm Excluded |
| Increased Lung Volumes |
| Left Costophrenic Angle Not Included |
| Left Shoulder Excluded |
| Limited by Motion |
| Low Lung Volumes |
| Lungs Not Fully Included |
| Meets All Technical Criteria |
| Non-Diagnostic |

TABLE 1-continued

Listing of Technical Defects

Right Costophrenic Angle Not Included
Right Shoulder Excluded

Figure 2A:
FIGS. 2A-2C are chest radiographs illustrating different technical defects.
Figure 2B:
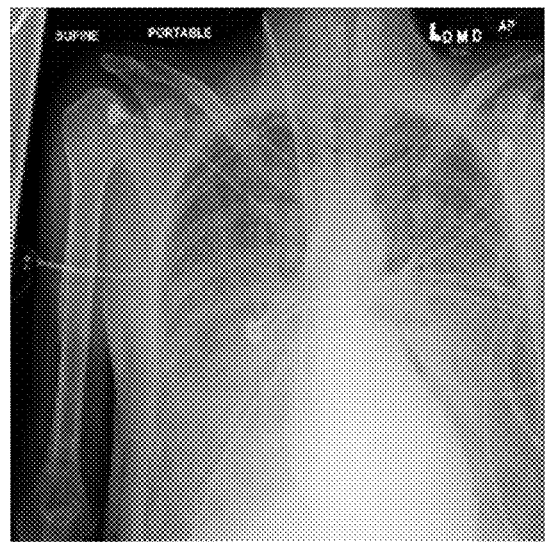
Figure 2C:
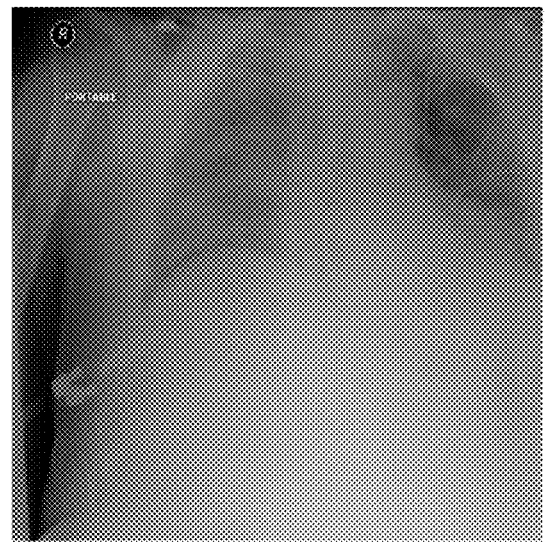

FIGS. 2A-2C are example chest radiographs illustrating different technical defects. FIG. 2A illustrates a chest radiograph that is considered diagnostically unacceptable because the left shoulder is excluded, the apices are not included, the left costophrenic angle is not included, the lungs are not fully included, the lung volume is low, and the right shoulder is excluded. FIG. 2B illustrates a chest radiograph that is diagnostically unacceptable because the diaphragm is excluded, the left shoulder is excluded, the costophrenic angles are not included, and the lungs are not fully included. FIG. 2C illustrates a chest radiograph that is diagnostically unacceptable because the left shoulder is excluded, the patient's body is rotated to the left, the apices are not included, the left costophrenic angle is not included, the patient's body is slanted to the left, the lung volume is low, the chest radiograph is limited by motion, and the lungs are not fully included. As a result of the illustrated technical defects, the medical images illustrated in FIGS. 2A-2C are considered diagnostically unacceptable and would, in practice, be rejected and repeated.

In one embodiment, the training data includes a dataset of 3,487 anterior-posterior ("AP") randomly sampled from the NIH CXR dataset of 112, 120 images. The AP projection is often taken portably at the bedside outside the controlled environment of the radiology exam room and therefore, are more likely to have technical quality issues (i.e., technical defects). These images (from PACS systems) had initially passed technical quality assessment controls by the technicians but may have been subsequently rejected due to quality issues. To determine a classification for each image in the dataset, the images were manually re-interpreted by experienced radiologists as belonging to one of two categories: (a) diagnostically acceptable, which includes studies without technical limitations or with some limitations but remaining diagnostic without requiring a rescan, and (b) non-diagnostically acceptable ("non-diagnostic"), which includes studies where technical limitations were sufficiently limiting to warrant rescanning.

In some embodiments, technical defects identified in the images (leading to a particular classification) were also marked or identified. And any defects from Table 1 identified in an image were used by the radiologists to classify an image. In some embodiments, all images in which the different technical defects in Table 1 were marked and the images were classified as non-diagnostic were considered "non-diagnostic." The markings or identification of the technical defects in each image also allows for the breakdown of the technical defects that caused an image to be classified as non-diagnostic. In some embodiments, the radiologists adding this information to the training information considered what an expert would consider a diagnostically unacceptable X-ray without having access to any further information regarding the a patient, the reason for the scan, or the like. However, in other embodiments, the radiologists may access and use this additional information to provide further insight into whether an image is diagnostically acceptable.

For example, in some embodiments, the radiologists classifying the training information made their classifications based on at least two considerations for a diagnostic image: (a) whether key organs (e.g., lungs, heart, airways, diaphragm, or the like) were visible and their shadows were cast perpendicularly onto the X-ray film and (b) whether the technical assessment affects the true purpose of why they are imaged. For example, although condition (a) applies for most X-rays when detecting diagnostically acceptable images, some sub-optimal images may ultimately be passed on as long as the most likely diagnostic purposes were satisfied, such as depending on the patient condition or if it was a follow-up or a repeat scan to reassess disease progress. Accordingly, the radiologists classifying the dataset may access patient information, may infer patient information from the images, or a combination thereof. For example, in some cases the radiologists performing the manual classification may guess the indications for the X-ray exams from other disease processes and devices present in the images. Accordingly, in these situations, if the radiologist believes that the main indication for an exam was to assess device positioning and rule out complications after some common bedside procedures (e.g., inserting an endotracheal tube or intravascular catheter), then as long as the image quality is good enough for these main indications, the radiologist would not consider an X-ray non-diagnostic even when the images include minor technical defects, such as minor cut offs of costophrenic angle. This may be especially true when radiologists think most other radiologists would report on similar images for these indications and simply state the exams limitations (in the ultimate report). For example, under such situations, the harm of repeating the exam before reporting (discomfort to patient, delay in care, costs, and resource usage) outweighs the potential benefits (fewer limitations for the diagnostic claims of the exam). Furthermore, in some situations, depending on a patient condition, it may be difficult for a technician to get better quality images (e.g., the patient usually has severe diseases and is most likely bed-bound and surrounded by wires and other medical instruments).

In some embodiments, with respect to the classification methodology, the dataset is divided into training, validation, and test set using splits of 80%, 10%, and 10%, respectively, and a deep-learning network is then trained to distinguish between diagnostic and non-diagnostic studies using class weighting to account for the imbalanced classes. In some embodiments, the deep-learning network includes one or more deep convolutional neural networks ("CNNs"). CNNs learn the feature representations of the problem (e.g., a medical image) unsupervised based on the ground truth labels and appropriate loss functions. Further, the introduction of non-linearity at each layer adds to the combination of features that can be learned allowing for a very rich feature space of representations. CNNs generally outperform several traditional machine learning classifiers that required handcrafted features that need domain expertise.

In some embodiments, as described in more detail below, DenseNet-121 CNNs are used. DenseNet-121 CNNs have several advantages, including, for example, alleviating the vanishing-gradient problem, strengthening feature propagation, encouraging feature reuse, and substantially reducing the number of parameters. In each layer, the feature-maps of all preceding layers are used as inputs, and its own feature-maps are used as inputs into all subsequent layers.

In some embodiments, a combination of CNNs is used to build the classifier system consisting of DenseNet 121 and U-Net CNN networks. For example, FIG. 3 is a block diagram illustrating an exemplary combination of CNNs to create a final output of the classifier.

Figure 3:
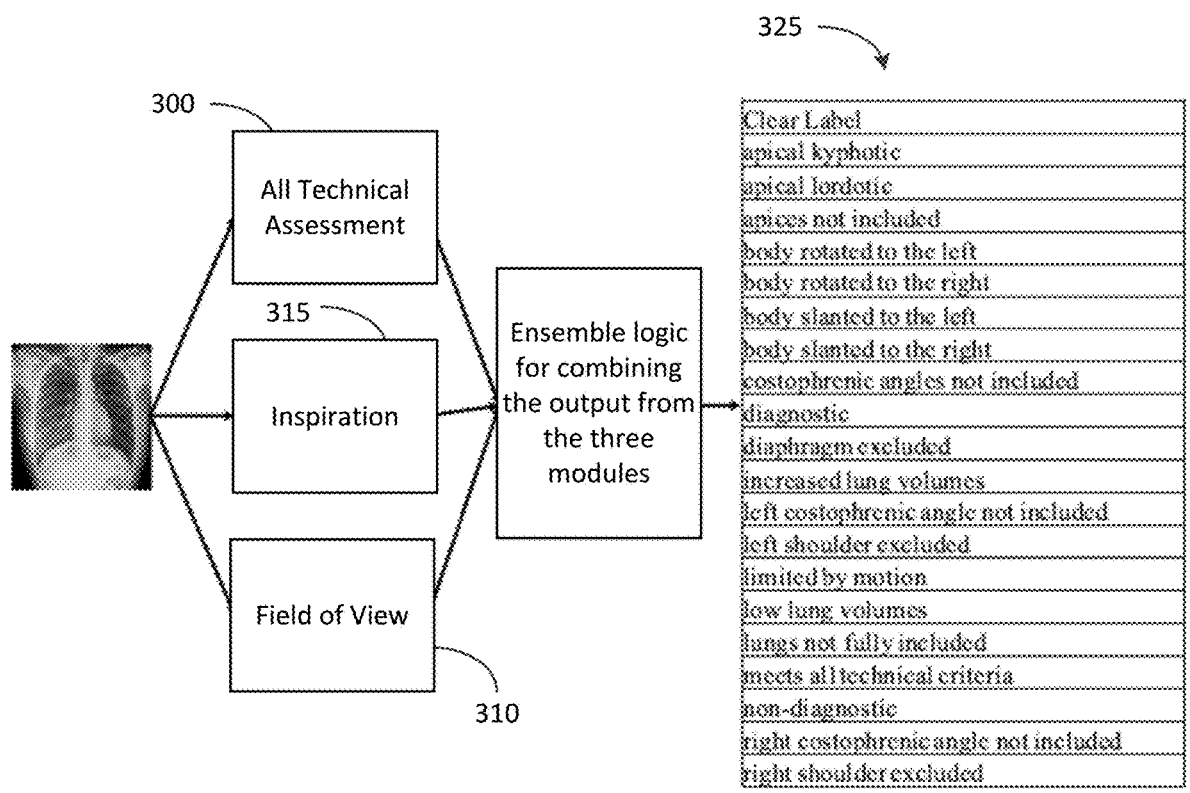
FIG. 3 is a block diagram illustrating an example combination of convolution neutral networks ("CNNs") to create a final output of a classifier according to some embodiments.

In some embodiments, an all technical assessment module 300 is trained using a DenseNet classifier on the 20 labels shown in FIG. 3. The network is pre-trained using a larger NIH dataset and fine-tuned using transfer learning on a subset of radiographs, which were annotated for technical assessment labels (as described above). In addition to the DenseNet end-to-end deep learning classifier, two specific rule-based classifiers may be developed for an inspiration module 315 and a field of view module 310.

The DenseNet enables a method of training deeper and more accurate networks primarily by connecting every layer to every other layer in a feed-forward fashion through a block of layers called the dense block. For each layer in the dense block, all the feature maps of the preceding layers are used as inputs and its own features generated are again used as inputs for the subsequent layers. This provides several advantages, such as alleviating the vanishing gradient problem, improves the feature propagation and reuse, and reducing the number of parameters.

Positional errors (i.e., field of view) is one of the most common reasons for rejection of radiographs. Therefore, to ensure robust identification of the field of view, another UNet based network may be used to provide additional verification (i.e., a field of view module 310), as illustrated in FIG. 3. Similarly, adequate inspiration may be an important issue when imaging radiographs. An improperly inspired lung would appear quite different leading to the wrong diagnosis. Hence, a separate UNet based inspiration module may be developed (i.e., an inspiration module 315), as illustrated in FIG. 3. The two UNet Networks classified a particular radiograph may be based off the segmentation plus rule-based inference.

Figure 4A:
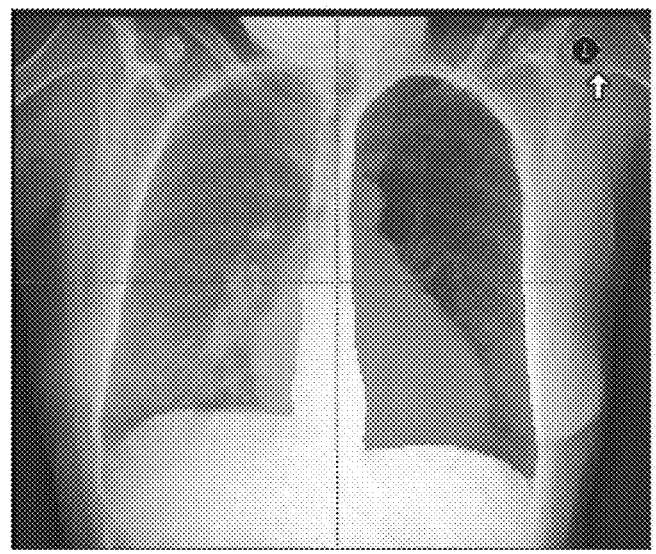
FIGS. 4A-4B illustrate example left lung and right lung label outputs.
Figure 4B:
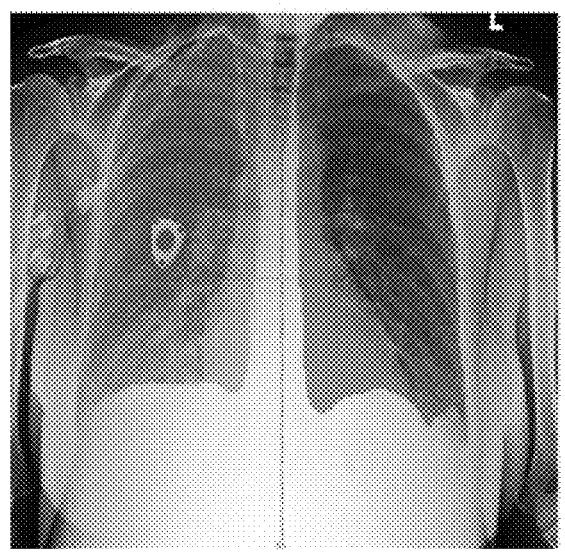

In some embodiments, the field of view module 310 contains a segmentation network and a logic. The segmentation network is trained on human-labeled annotations of the lung fields. The segmentation network is a UNet architecture. The input to the network is a chest X-ray image resized to 256×256 pixels and its output is left and right lung labels. For example, FIGS. 4A-4B illustrate example outputs from the trained network. The field of view module 310 may use these labels to create a bounding box of the lung. The field of view module 310 may use the following logic to come up with output flags: (a) if the bottom part of the left lung is close to the edge of the image (10 pixels) then the flag "left costophrenic angle is not included" is ON; (b) if the top part of the left lung is close to the edge of the image (10 pixels) then the flag "left shoulder is excluded" is ON; (c) if the bottom part of the right lung is close to the edge of the image (10 pixels) then the flag "right costophrenic angle is not included" is ON; (d) if the top part of the right lung is close to the edge of the image (10 pixels) then the flag "right shoulder is excluded" is ON; an (e) if any of the previous flags are ON the flag or the right part of the left lung is close to the edge of the image (10 pixels) or the left part of the right lung is close to the edge of the image (10 pixels) "lungs not fully included" is ON, where Left lung or Right lung are based on the human anatomy orientation and not the viewer.

Figure 5A:
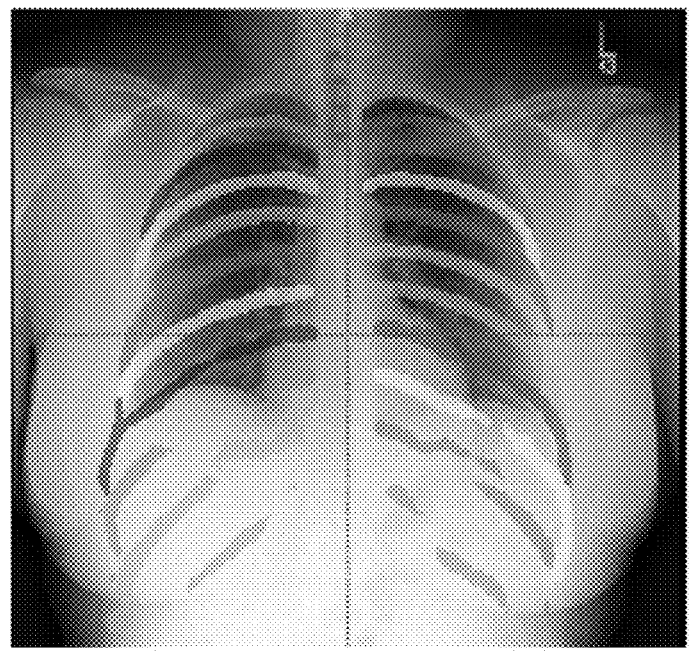
FIGS. 5A-5B illustrate example rib segmentation outputs.
Figure 5B:
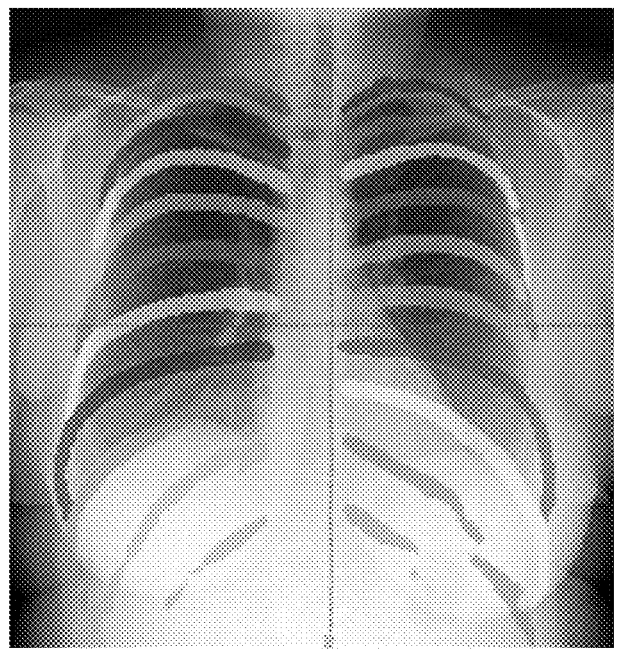
Figure 6A:
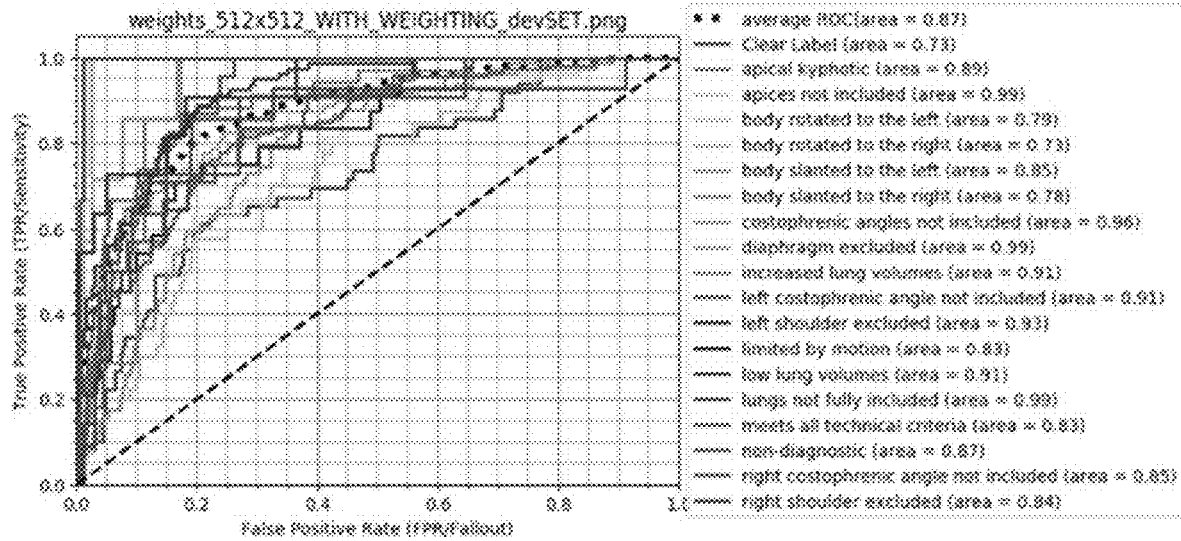
FIGS. 6A-6D are graphs illustrating a receiver operating curve and a precision-recall curve for 21 label classification for testing and validation datasets.
Figure 6B:
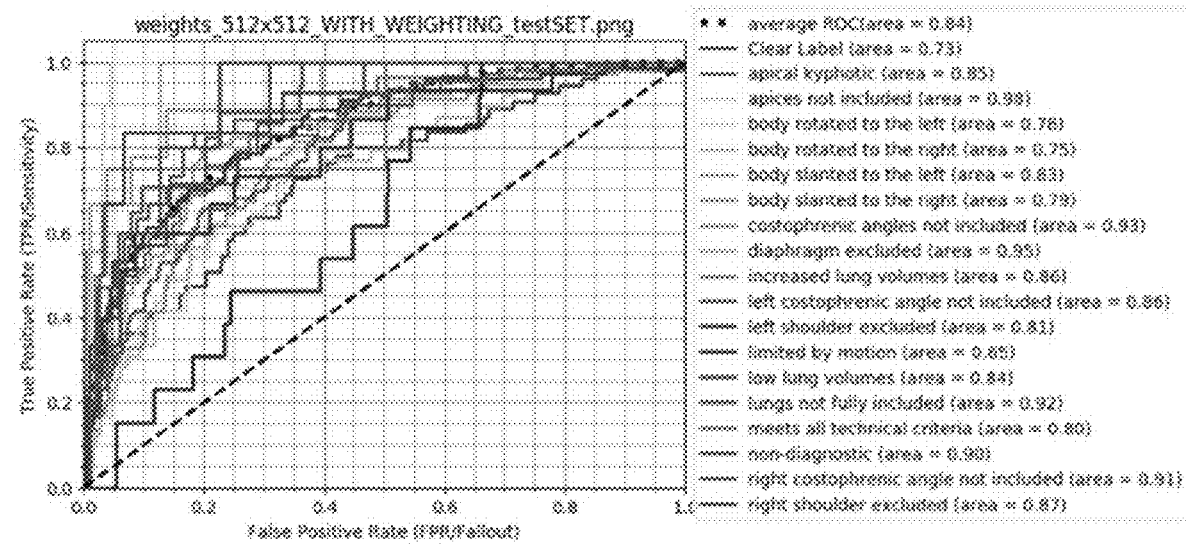
Figure 6C:
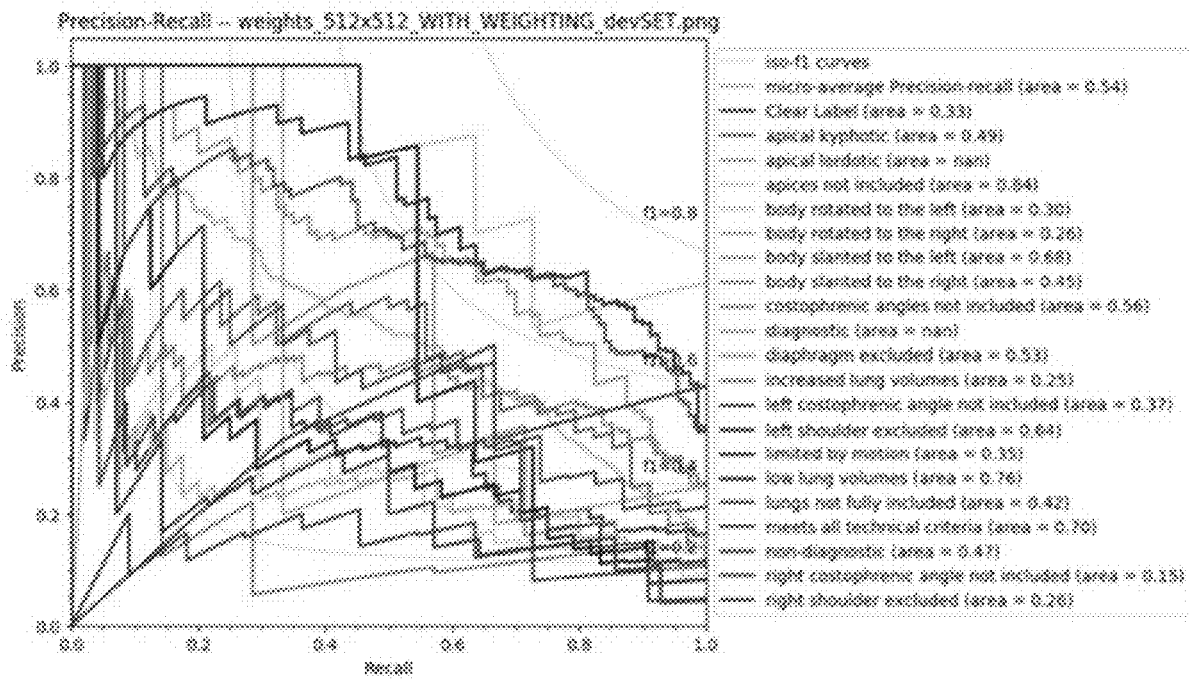
Figure 6D:
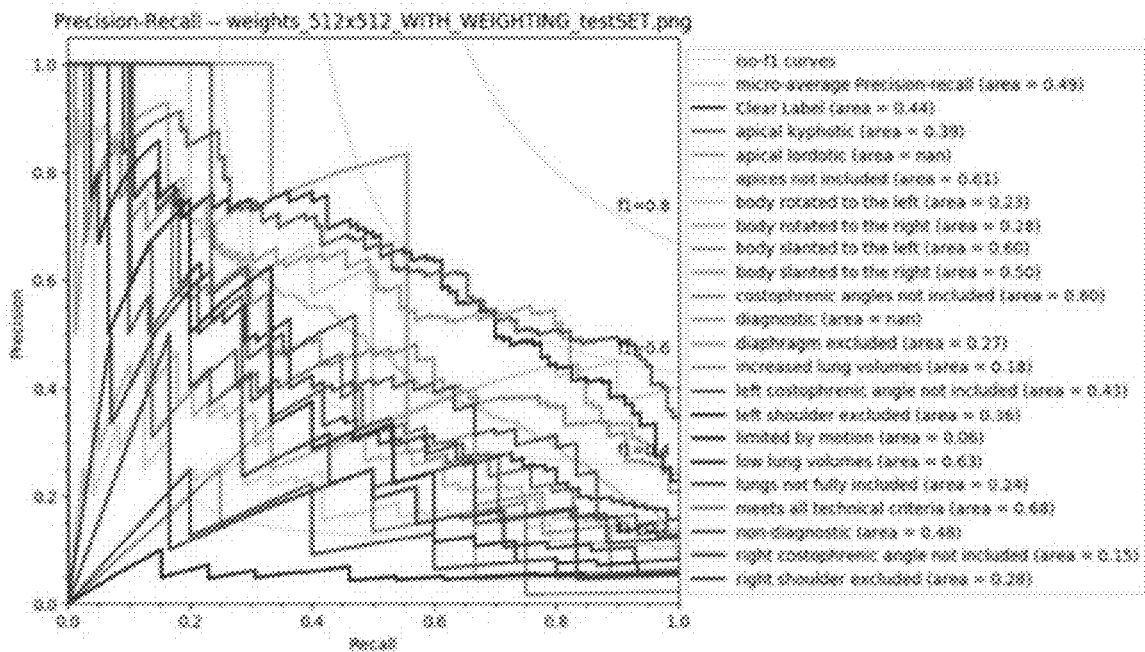
Figure 7A:
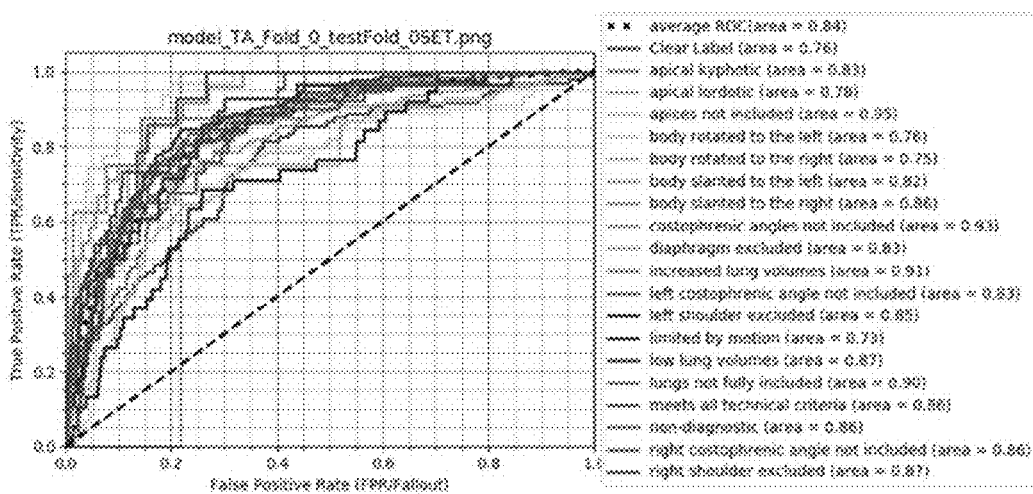
FIGS. 7A-7J are graphs illustrating a five-fold cross validation of label classifications.
Figure 7B:
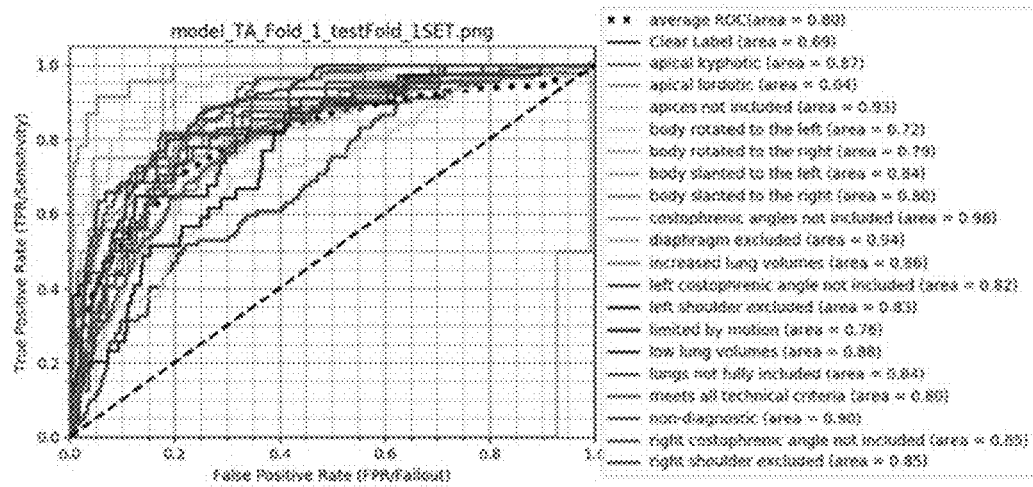
Figure 7C:
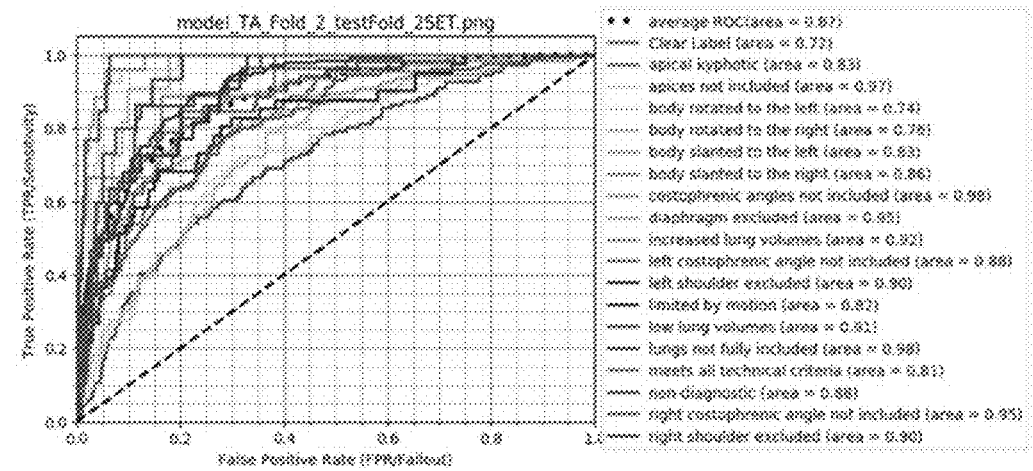
Figure 7D:
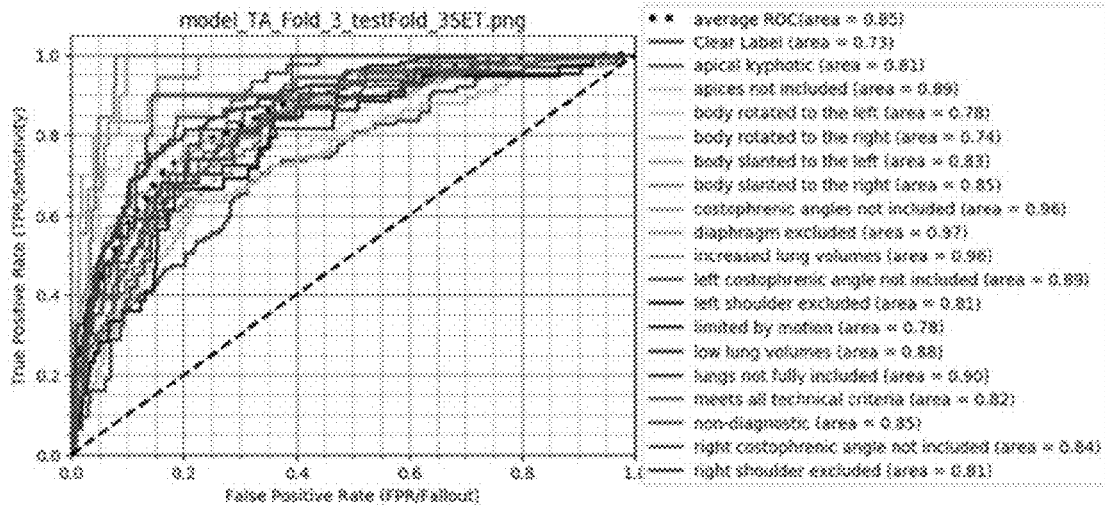
Figure 7E:
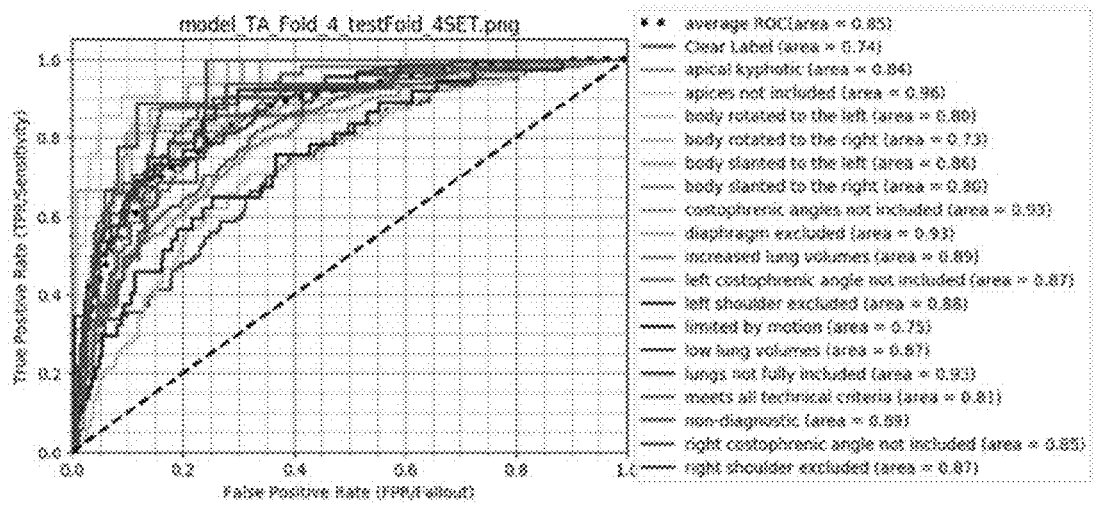
Figure 7F:
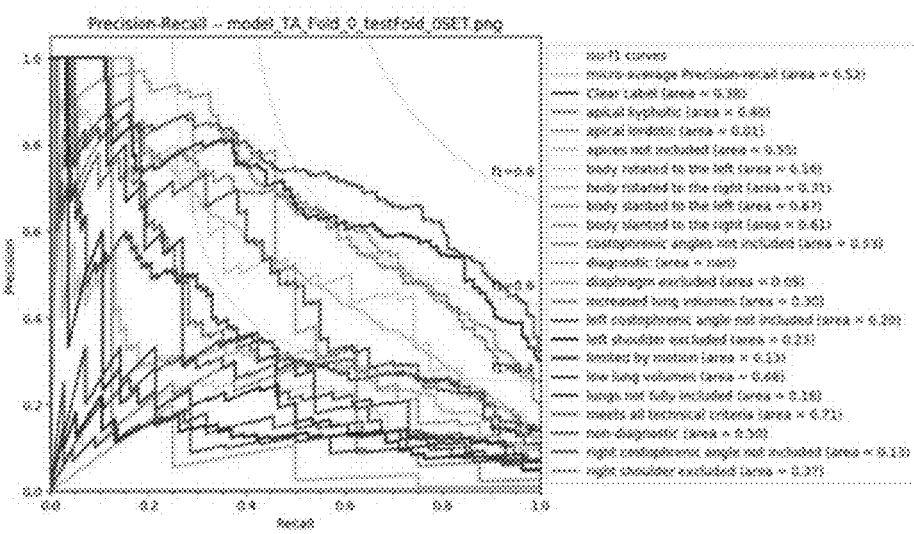
Figure 7G:
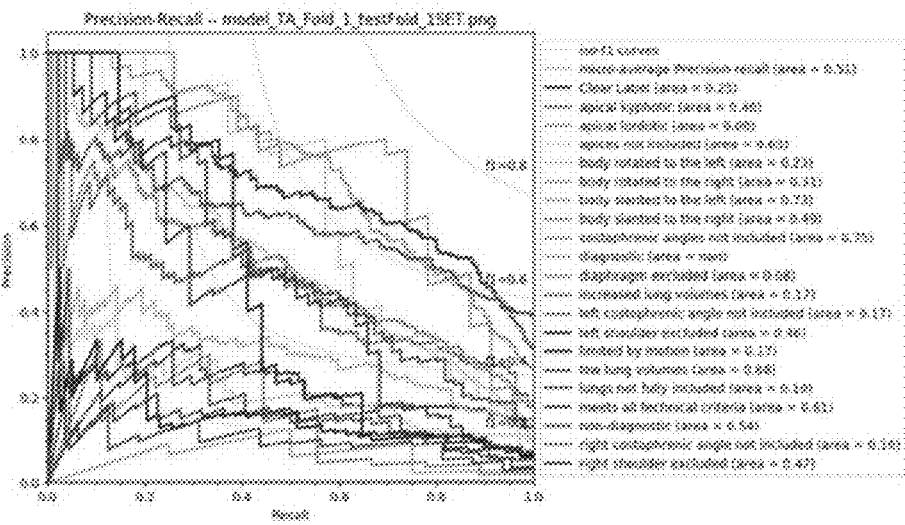
Figure 7H:
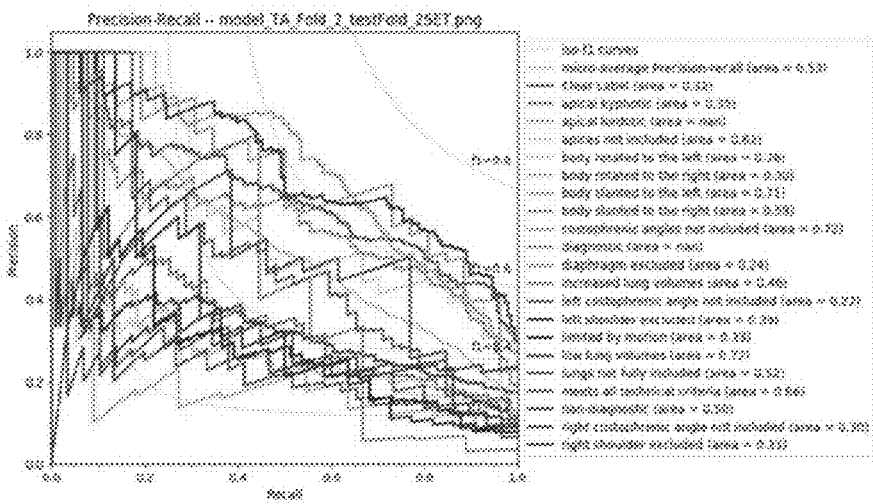
Figure 7I:
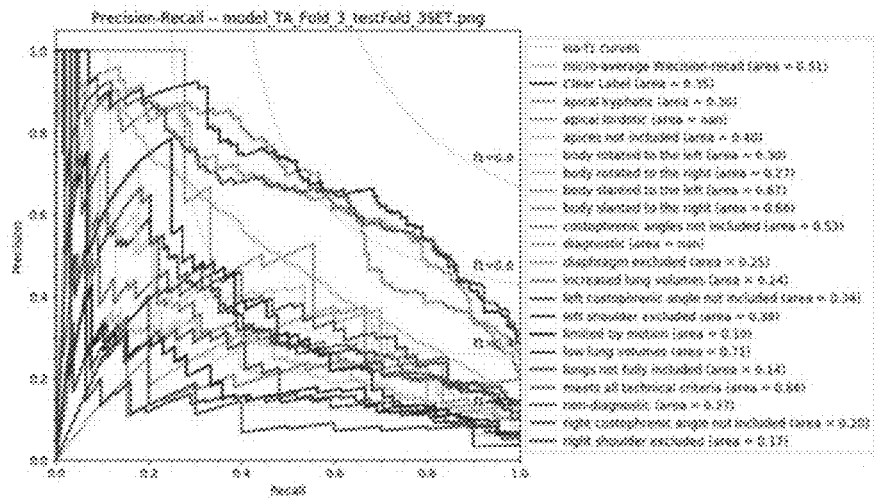
Figure 7J:
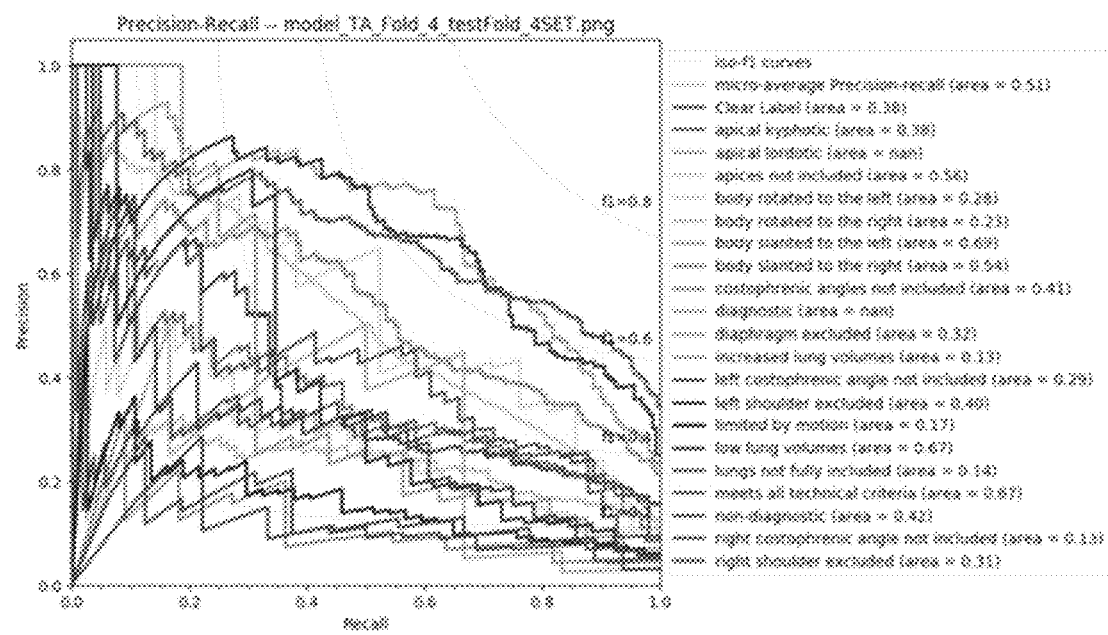

In some embodiments, the inspiration module 315 contains a segmentation network and a logic. The segmentation network is trained on human-labeled annotations of the rib bones. The segmentation network is a UNet architecture. The input to the network is a chest X-ray image resized to 256×256 pixels and its output are labels for all visible ribs as well as the lung fields. The inspiration module 315 may use the following logic to come up with output flags: (a) if the number of ribs is above 25 or less than 4, then the "non-diagnostic" flag is ON; and (b) for each lung field (i.e., left and right): (i) if there are more than 10 (i.e., >10) ribs inside the lung field then the "increased lung volumes" flag is ON; (ii) if there are exactly 10 ribs (i.e., =10) inside the lung field then "diagnostic" flag is ON; and (iii) if there are less than 10 ribs (i.e., <10) inside the lung field then "low lung volumes" flag is ON. FIGS. 5A-5B illustrate example rib segmentation outputs from a UNet architecture used to build logic for the inspiration module.

In some embodiments, the all technical assessment module 300, the field of view module 310, and the inspiration module 315 are combined to produce a unified output of 21 labels 325, such as those listed in Table 1. The main network is the all technical assessment module 300, and, if the output probabilities are two standard deviations below the specified threshold for those labels with outputs from more than one module, the output from the all technical assessment module 300 is ignored and the outputs from the field of view module 310 and the inspiration module 315 are considered. However, if the overall all technical assessment module 300 produces a non-diagnostic output, then everything from the inspiration module 315 and the field of view module 310 are ignored.

The transfer learned DenseNet121 used in some embodiments may be pre-trained on the Image Net dataset. The input images may be re-sized to 512×512×3. To reuse the existing weights of the pre-trained dataset that were trained on images of size 224×224×3, the last fully connected layer can be dropped and the global average pooling layer (name=avg pool in keras) is outputted followed by fully connected sigmoid output layer. The network may be fine-tuned end-to-end using an Adam optimizer with a learning rate of 0.0001 and a binary cross-entropy loss function. The learning rate may be reduced by a factor of (0.1*learning rate) every time the validation metric stopped improving. In some embodiments, the network is optimized with an upper limit set to 200 epochs. However, the reduced learning rate makes the learning rate negligibly small by the end, thus preventing overfitting on the training data.

Figure 8A:
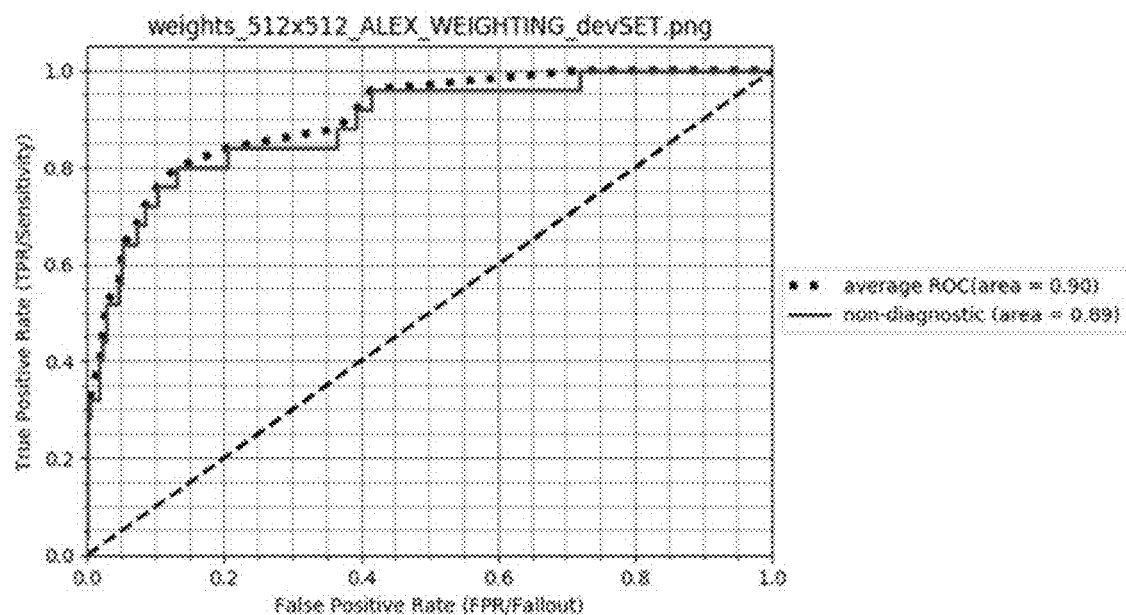
FIGS. 8A-8D are graphs illustrating a receiver operating curve and a precision-recall curve for binary non-diagnostic and diagnostic classification for testing and validation datasets.
Figure 8B:
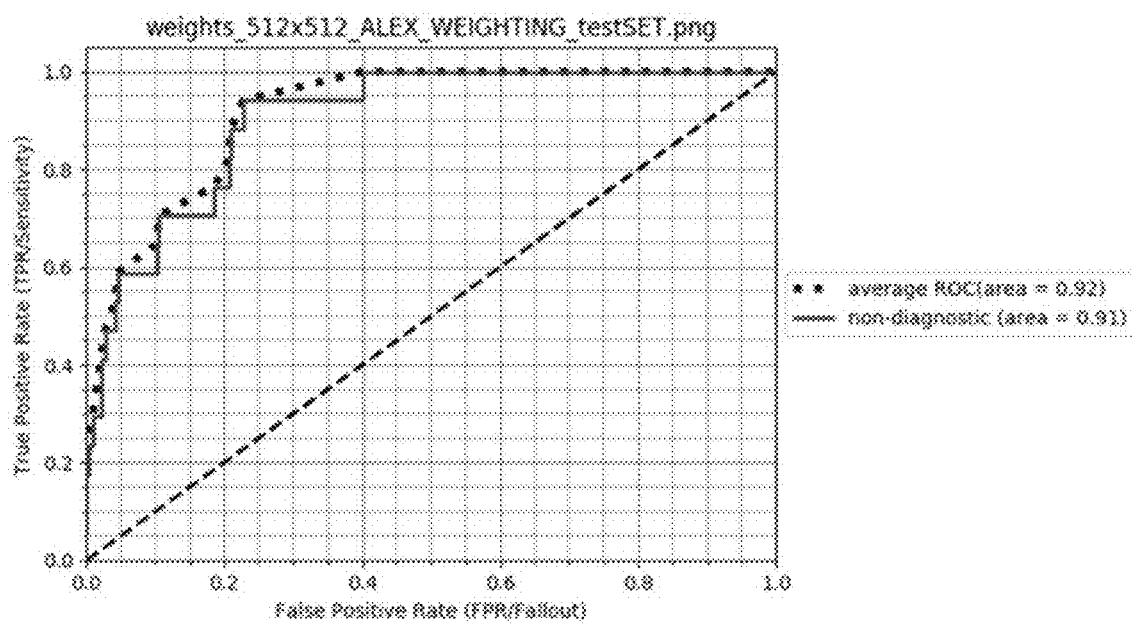
Figure 8C:
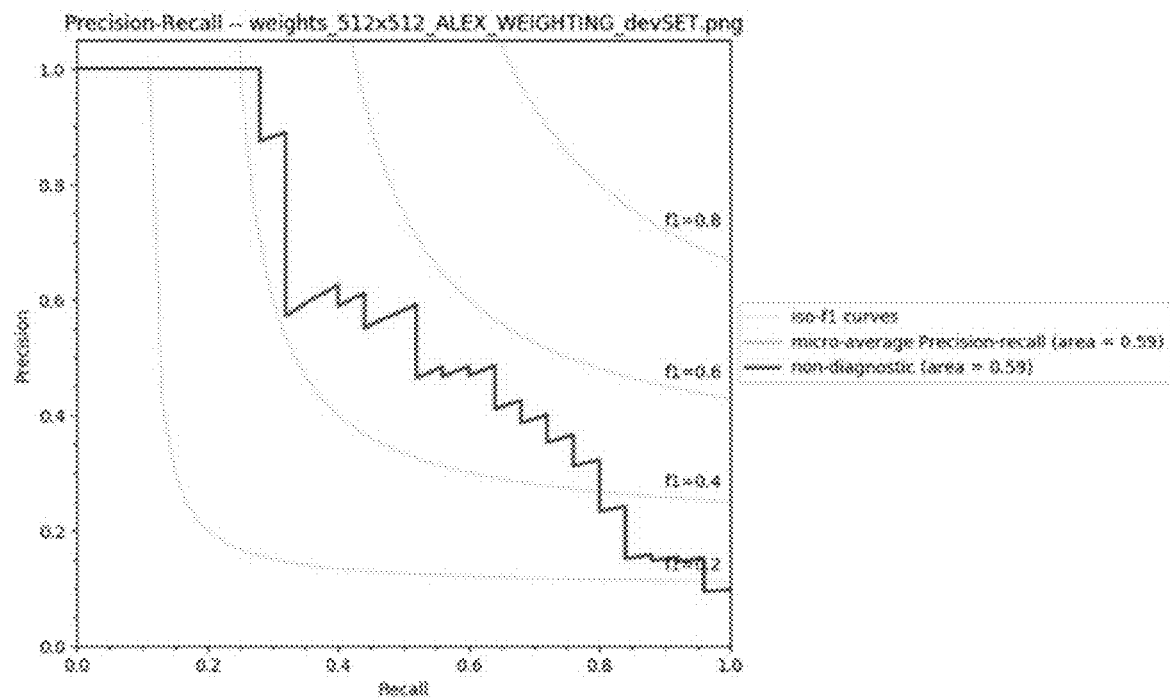
Figure 8D:
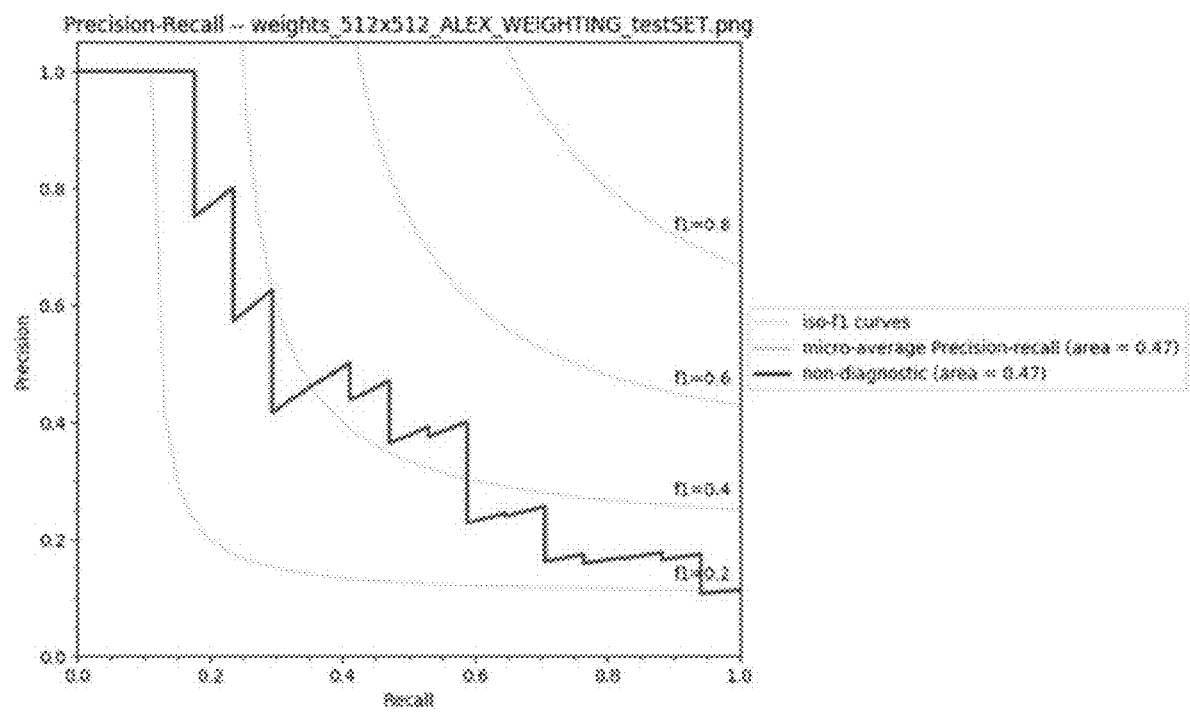

From the ground truth annotations of 3,487 studies, 500 (14.3%) studies were marked as free of technical limitations, 268 (7.7%) were non-diagnostic, and 2719 (78%) had some technical limitations but were considered adequate for interpretation. The trained AI algorithm, thus, in some embodiments, is configured to recognize 238 of the non-diagnostic studies with 100% specificity with an overall sensitivity and specificity defined with an area under the receiver operator curve ("ROC") of 0.93, as illustrated in FIGS. 8A and 8B.

It should be understood that different types and configurations of machine learning techniques may be used to develop the classification model. For example, all 21 technical defect labels may be classified using the DenseNet algorithm only. In this embodiment, the dataset can be broken down into training (80%), validation (10%), and testing (10%) resulting in 2,788, 348, 351 patients, respectively. In this embodiment, the DenseNet can consist of 121 layers with an Adam optimization and a sigmoid activation for classification with a binary cross-entropy loss function. To account for the imbalanced classes, the class weighting, which may be the inverse of the number of training examples of each class, may be added. To further validate, a five-fold cross validation may be designed with the datasets split into training and testing of 2,790 and 697 patients.

For example, FIGS. 6A-6D shows classifying all 21 labels using the DenseNet-121. The ROC and the precision-recall ("PR") curve is plotted for the validation (N=348) and training (N=351) dataset. The average ROC were 0.87 and 0.84, respectively, indicating good overall accuracy. In some embodiments, depending on the use case and the specific disease detection, the system could be tuned to set the operation point on this curve to achieve the desired sensitivity and specificity.

As noted above, to validate the entire dataset, a five-fold validation experiment may be run. FIGS. 7A-7J shows the ROC and the PR curve for each of the five-folds. In particular, FIGS. 7A-7J are graphs illustrating the five-fold cross validation of the 21 label classifications on the entire dataset where the split for training/testing is 2,790/697 subjects, respectively. The five-fold mean of average ROCs: 0.842 with the Min/Max: 0.80/0.87 and SD: 0.025. The lowest average ROC of 0.80 in fold 2 may be due to a lack of sufficient data in the apical kyphotic class, which, in this specific embodiment, had a total of three cases overall.

A binary classifier system may also be designed and tested to identify the non-diagnostic versus diagnostic radiographs. To prepare the dataset labels, the non-diagnostic class may be kept as-is while the other 20 technically acceptable labels may be merged into a single class resulting in 268 images with non-diagnostic labels and 3,219 images with diagnostic labels. The same 80%, 10%, 10% split may be used to train, validate, and test the dataset. In some embodiments, a DensNet-121 can also be trained using the same configuration as described above. In some embodiments, the implementation may be done, for example, in Python using Keras with Tensorflow backed for the deep learning algorithms and SciKit-learn for the statistical analysis.

In some embodiments, to test the system as a binary classification system of detecting non-diagnostic cases the labels may be modified using the same DensNet-121 with binary label output. For example, FIGS. 8A-8D shows the validation and the testing set ROC and PR curves with both achieving much higher ROCs and PRs compared to the 21 label cases.

The increasing clinical demands on radiographers and radiologists make it imperative to operate as efficiently as possible to provide the highest quality of care to patients. These results suggest that the AI quality assessment could potentially reduce repeat chest radiograph rate by 89% by providing feedback for non-diagnostic studies earlier in the radiology workflow at the point of care itself.

After generating one or more classification models, the models can be stored to the classification model database 250, which can be used at the point of imaging (the medical imaging device 215) to automatically detect or determine diagnostically unacceptable images at the point of imaging, which can reduce re-captures and associated wastes and inefficiencies.

Figure 9:
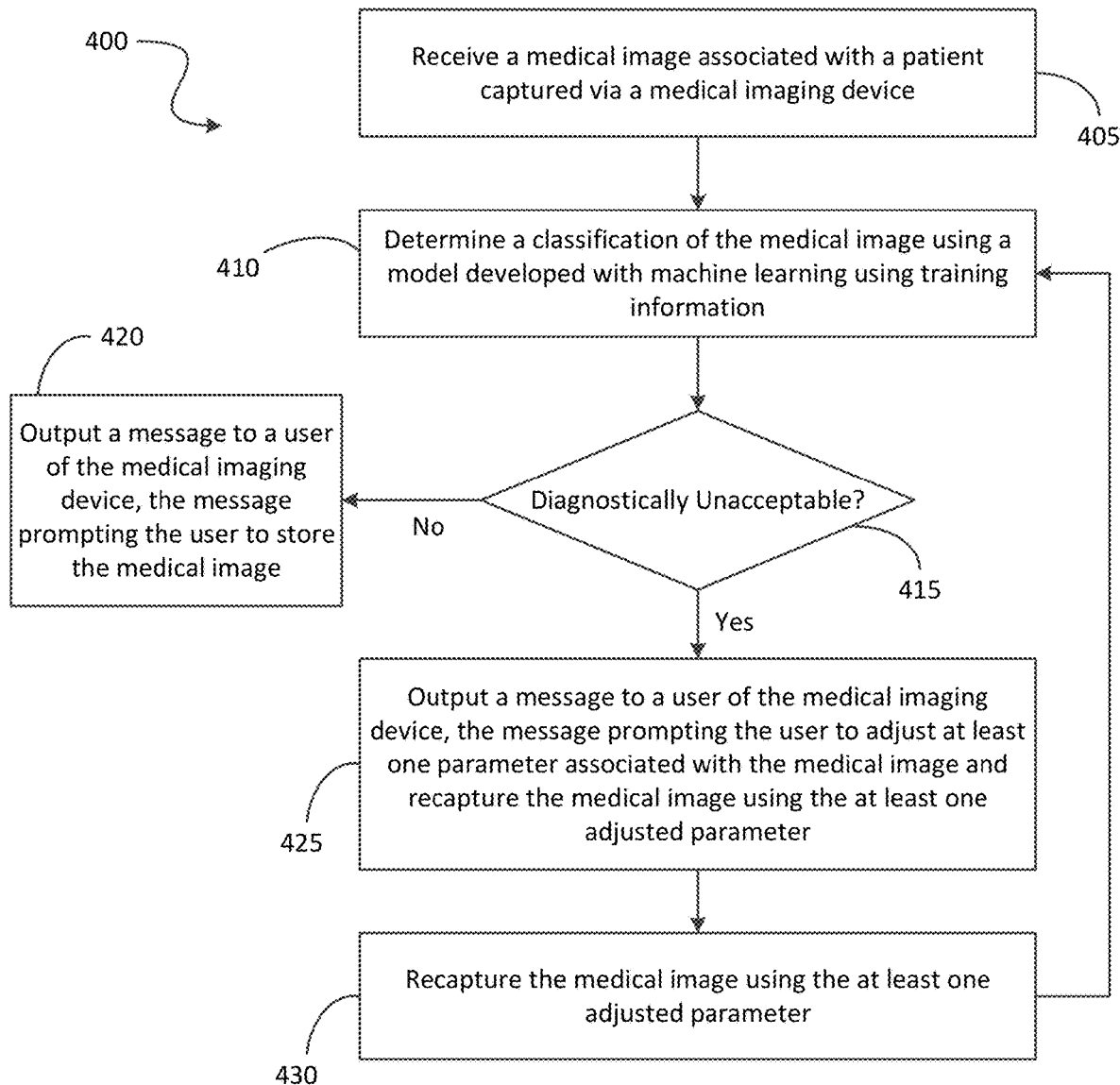
FIG. 9 is flowchart illustrating a method of determining a diagnostically unacceptable image using the system of FIG. 1 according to some embodiments.

For example, FIG. 9 is a flowchart illustrating a method 400 for determining a diagnostically unacceptable medical image (for example, a medical image 265) according to some embodiments. The method 400 is described here as being performed by the medical imaging device 215 (via an electronic processor executing instructions). However, as noted, above, portions of the functionality performed by the medical imaging device 215 (or a portion thereof) may be performed by other devices, including, for example, the server 205 (via the electronic processor 225 executing instructions).

As illustrated in FIG. 9, the method 400 includes receiving a medical image captured via the medical imaging device 215, wherein the medical image is associated with a patient (at block 405). As noted above, a technician may use the medical imaging device 215 to capture one or more medical images associated with a patient, such as an AP chest radiograph.

After receiving the medical image, the medical imaging device 215 (with at least one electronic processor) determines a classification of the medical image using a model developed with machine learning using training information as described above (at block 410). The model may include one or more of the classification models stored in the classification model database 250. As noted above, in some embodiments, the classification model database 250 is stored in a memory of the medical imaging device 215. However, in other embodiments, the classification model database 250 is stored in the memory 230 of the server 205. In such embodiments, the medical imaging device 215 (i.e., an electronic processor of the medical imaging device 215) accesses one or more of the classification models stored in the classification model database 250 of the server 205 via the communication network 220. For example, the medical imaging device 215 may provide the captured medical images to the server 205 for classification using one of the classification models.

In some embodiments, the medical imaging device 215 (i.e., an electronic processor of the medical imaging device 215) determines the classification of the medical image by analyzing content of the medical image with the model to identify whether the medical image includes one or more technical defects, such as the technical defects listed in Table 1. For example, the model may be used to identify whether the medical image includes an excluded body part of the patient, an inclusion of a partial body part of the patient, an improper lung volume of the patient, an improper viewing angle of the first medical image, an improper exposure, and the like. As noted above, in some embodiments, the classification of the medical image is based on whether the medical image includes one or more technical defects. For example, when the medical image does not include a technical defect, the medical image is classified as diagnostically acceptable. However, when the medical image includes one or more technical defects, the medical image is classified as diagnostically unacceptable. In other embodiments, the medical image is classified as diagnostically unacceptable when a total number of technical defects of the medical image exceeds a predetermined threshold. Alternatively or in addition, in some embodiments, the medical image is classified as diagnostically unacceptable based on which technical defects are identified in the medical image or other rules or thresholds.

As illustrated in FIG. 9, when the medical image is classified as being diagnostically acceptable ("No" at block 415), the medical imaging device 215 (i.e., an electronic processor of the medical imaging device 215) may output, via the display device 260 of the medical imaging device 215, a message prompting the technician to store (or accept) the medical image (at block 420). For example, the medical imaging device 215 may prompt the technician to accept and store the medical image, such as in the medical image database 210.

Alternatively, when the medical image is classified as being diagnostically unacceptable ("Yes" at block 415), the medical imaging device 215 (i.e., an electronic processor of the medical imaging device 215) outputs, via the display device 260 of the medical imaging device 215, a message prompting the technician to adjust at least one parameter associated with the medical image and to recapture the medical image using the at least one adjusted parameter (at block 425). The parameter associated with the medical image may relate to a parameter associated to the patient, a parameter associated with the medical imaging device 215, or a combination thereof. For example, a parameter associated with the patient may include an orientation of the patient, a position of the patient, a lung volume of the patient, or the like. A parameter associated with the medical imaging device 215 may include, for example, an operating parameter of the medical imaging device 215, such as a parameter controlling an exposure for the medical image.

In some embodiments, the medical imaging device 215 also outputs, via the display device 260, the classification of the medical image indicating whether the medical image is diagnostically unacceptable or diagnostically acceptable. The medical imaging device 215 may output a preview of the medical image to the technician. In some embodiments, the preview may include a preview image of the medical image that includes one or more technical defect labels or markers identifying each technical defect associated with the medical image. Alternatively or in addition, when the medical image is classified as being diagnostically unacceptable, the medical imaging device 215 may provide instructions to the technician pertaining to how to correct the diagnostic acceptability of the medical image (what parameter to change and/or how to change the parameter). In some embodiments, the medical imaging device 215 may also automatically make adjusts to the parameters as recommended (e.g., before or after confirmation of the adjustment by the technician). Alternatively or in addition, when the medical image is classified as being diagnostically unacceptable, the medical imaging device 215 may provide a listing of the one or more technical defects of the medical image.

After prompting the technician to adjust the at least one parameter associated with the medical image and to recapture the medical image using the at least one adjusted parameter (at block 425), the technician controls the medical imaging device 215 to recapture the medical image (e.g., capture a second medical image) using the at least one adjusted parameter (at block 430). As illustrated in FIG. 9, after the medical image is recaptured, the method 400 returns to block 410 to determine a classification of the recaptured medical image and this process can continue until diagnostically acceptable images are captured (or the technician decides that better images cannot be captured).

In some embodiments, the medical imaging device 215 also receives (via the human-machine interface 240) feedback associated with the classification of a medical image and updates one or more of the classification model based on the feedback. For example, the technician may provide feedback via the human-machine interface 240 of the medical imaging device 215. In some embodiments, the feedback indicates whether the technician believed that the classification of the medical image was correct. The feedback may be used as further training data to update one or more classification models stored in the classification model database 250. Radiologists reading images may similarly provide feedback, which may be used to update the classification models. For example, if an image study reaches a radiologist and the radiologist rejects the study and requests a rescan, this information can be used to update a classification model that originally classified the images in the study as diagnostically-acceptable.

Thus, embodiments described herein provide systems and methods for determining or detecting diagnostically unacceptable images at the point of image acquisition using machine learning functionality to avoid wastes and inefficiencies resulting from requiring a subsequent recapture of images.

Various features and advantages of the embodiments described herein are set forth in the following claims.

What is claimed is:

1. A system for determining a diagnostically unacceptable medical image, the system comprising:
at least one electronic processor configured to
receive a new medical image captured via a medical imaging device, a new medical image associated with a patient;
determine a classification of the new medical image using a model developed with machine learning using training information, the training information including a plurality of medical images and an associated classification for each of the plurality of medical images, each associated classification identifying whether the associated medical image is diagnostically unacceptable, wherein the classification of the new medical image indicates whether the new medical image is diagnostically unacceptable, wherein the electronic processor determines the classification of the new medical image by analyzing content of the new medical image with the model to identify one or more technical defects in the new medical image and wherein the electronic processor classifies the new medical image as diagnostically unacceptable when a total number of the one or more technical defects of the new medical image exceeds a predetermined threshold; and
when the classification of the new medical image indicates that the new medical image is diagnostically unacceptable, prompt the user of the medical imaging device to
adjust a parameter associated with the new medical image, and
recapture the new medical image using the adjusted parameter.

2. The system of claim 1, wherein the at least one electronic processor is further configured to, when the classification indicates that the new medical image is diagnostically acceptable, prompt the user of the medical imaging device to store the new medical image.

3. The system of claim 1, wherein the parameter associated with the new medical image includes at least one selected from a group consisting of a parameter associated with the patient and a parameter associated with the medical imaging device.

4. The system of claim 3, wherein the parameter associated with the patient includes at least one selected from a group consisting of an orientation of the patient, a position of the patient, and a lung volume of the patient.

5. The system of claim 1, wherein the at least one electronic processor is further configured to receive feedback associated with the classification of the new medical image and update the classification model based on the feedback.

6. The system of claim 1, wherein the one or more technical defects include at least one selected from a group consisting of an excluded body part of the patient, an inclusion of a partial body part of the patient, an improper lung volume of the patient, and an improper viewing angle of the medical image.

7. The system of claim 1, wherein the electronic processor is further configured to output, via the display device of the medical imaging device, a preview of the new medical image to the user of the medical imaging device, wherein the preview includes one or more technical defect labels, each technical defect label identifying one of the one or more technical defects associated with the new medical image.

8. The system of claim 1, wherein the machine learning includes at least one deep convolutional neural network.

9. A method of determining a diagnostically unacceptable medical image, the method comprising:
receiving, with at least one electronic processor, a first medical image captured via a medical imaging device, the first medical image associated with a patient;
determining, with the at least one electronic processor, a classification of the first medical image using a model developed with machine learning using training information, the training information including a plurality of medical images and an associated classification for each of the plurality of medical images, each associated classification identifying whether the associated medial image is diagnostically unacceptable, wherein the classification of the first medical image indicates that the first medical image is diagnostically unacceptable, wherein determining the classification of the first medical image includes analyzing content of the first medical image with the model to identify one or more technical defects in the first medical image and classifying the first medical image as diagnostically unacceptable when a total number of the one or more technical defects of the first medical image exceeds a predetermined threshold
outputting, via a display device of the medical imaging device, a first message to a user of the medical imaging device, the first message prompting the user to adjust at least one parameter associated with the first medical image and to capture a second medical image using the at least one adjusted parameter;
receiving the second medical image captured via the medical imaging device using the at least one adjusted parameter;
determining, with the at least one electronic processor, a classification of the second medical image using the model, the classification of the second medical image indicating that the second medical image is diagnostically acceptable; and
outputting, via the display device, a second message to the user of the medical imaging device, the second message prompting the user to store the second medical image.

10. The method of claim 9, further comprising:
outputting, via the display device, a preview of the first medical image to a user of the medical imaging device, wherein the preview includes one or more technical defect labels, each technical defect label identifying one of the one or more technical defect associated with the first medical image.

11. The method of claim 10, wherein outputting the first message to the user includes outputting one or more instructions to the user of the medical imaging device, the one or more instructions providing instructions to the user of the medical imaging device one how to correct the one or more technical defects associated with the first medical image.

12. The method of claim 9, wherein analyzing the content of the first medical image with the model to identify the one or more technical defects includes analyzing the content of the first medical image with the model to identify whether the first medical image includes at least one selected from a group consisting of an excluded body part of the patient, an inclusion of a partial body part of the patient, an improper lung volume of the patient, and an improper viewing angle of the first medical image.

13. A non-transitory, computer-readable medium storing instructions that, when executed by an electronic processor, perform a set of functions, the set of functions comprising:
receiving a first medical image captured via a medical imaging device, the first medical image associated with a patient;
determining a classification of the first medical image using a model, the classification indicating whether the first medical image is diagnostically unacceptable, wherein determining the classification of the first medical image includes analyzing content of the first medical image with the model to identify one or more technical defects in the first medical image and classifying the first medical image as diagnostically unacceptable when a total number of the one or more technical defects of the first medical image exceeds a predetermined threshold, the model developed based on training information, the training information including a plurality of medical images and an associated classification for each of the plurality of medical images, each associated classification identifying whether the associated medical image is diagnostically unacceptable; and
outputting a message, the message prompting a user, based on the classification of the first medical image, to either (a) store the first medical image or (b) adjust a parameter associated with the first medical image and capture a second medical image based on the adjusted parameter.

14. The computer-readable medium of claim 13, wherein the message prompts the user to adjust the parameter associated with the first medical image and capture the second medical image based on the adjusted parameter when the classification of the first medical image indicates that the first medical image is diagnostically unacceptable.

15. The computer-readable medium of claim 14, wherein, when the classification of the first medical image indicates that the first medical image is diagnostically unacceptable, the set of functions further includes:
determining a classification of the second medical image using the model; and
outputting a second message to the user, the second message prompting the user, based on the classification of the second medical image, to either (a) store the second medical image or (b) adjust a parameter associated with the second medical image and capture a third medical image based on the adjusted parameter associated with the second medical image.

16. The computer-readable medium of claim 13, wherein the message prompts the user to store the first medical image when the classification indicates that the first medical image is diagnostically acceptable.

17. The computer-readable medium of claim 13, wherein the adjusted parameter includes at least one selected from a group consisting of a parameter associated with the patient and a parameter associated with the medical imaging device.

* * * * *